US011965894B2

(12) United States Patent
Poynard

(10) Patent No.: US 11,965,894 B2
(45) Date of Patent: Apr. 23, 2024

(54) METHOD OF DIAGNOSIS OF DRUG INDUCED LIVER INJURY

(71) Applicants: BIOPREDICTIVE, Paris (FR); ASSISTANCE PUBLIQUE—HOPITAUX DE PARIS, Paris (FR)

(72) Inventor: Thierry Poynard, Paris (FR)

(73) Assignees: BIOPREDICTIVE, Paris (FR); ASSISTANCE PUBLIQUE-HOPITAUX DE PARIS, Paris (FR)

( * ) Notice: Subject to any disclaimer, the term of this patent is extended or adjusted under 35 U.S.C. 154(b) by 1053 days.

(21) Appl. No.: 16/489,426

(22) PCT Filed: Mar. 6, 2018

(86) PCT No.: PCT/EP2018/055508
§ 371 (c)(1),
(2) Date: Aug. 28, 2019

(87) PCT Pub. No.: WO2018/162502
PCT Pub. Date: Sep. 13, 2018

(65) Prior Publication Data
US 2020/0011879 A1 Jan. 9, 2020

(30) Foreign Application Priority Data
Mar. 7, 2017 (EP) ..................... 17305242

(51) Int. Cl.
*G01N 33/68* (2006.01)
*G16B 20/00* (2019.01)
*G16B 20/20* (2019.01)
*G16B 40/00* (2019.01)

(52) U.S. Cl.
CPC ......... *G01N 33/6893* (2013.01); *G16B 20/00* (2019.02); *G16B 20/20* (2019.02); *G16B 40/00* (2019.02); *G01N 2800/085* (2013.01); *G01N 2800/60* (2013.01)

(58) Field of Classification Search
CPC ......... G01N 33/6893; G01N 2800/085; G01N 2800/60; G16B 20/00; G16B 40/00
See application file for complete search history.

(56) References Cited

U.S. PATENT DOCUMENTS

2011/0256561 A1  10/2011 Soga et al.

FOREIGN PATENT DOCUMENTS

EP  1311857 B1  3/2006
WO  2010025410 A2  3/2010

OTHER PUBLICATIONS

International Search Report and Written Opinion dated May 3, 2018 for corresponding PCT Application No. PCT/EP2018/055508.
Poynard T. et al., "Applicability and precautions of use of liver injury biomarker FibroTest. A reappraisal at 7 years of age", BMC Gastroenterology, vol. 11, No. 1, 2011, pp. 1-11 XP021098125.
Munteanu M. et al., "Diagnostic performance of FibroTest, SteatoTest and ActiTest in patients with NAFLD using the SAF score as histological reference", Aliment Pharmacol Ther., vol. 44, No. 8, 2016, pp. 877-889 XP055327194.
Poynard T. et al., "Impact of adefovir dipivoxil on liver fibrosis and activity assessed with biochemical markers (FibroTest-ActiTest) in patients infected by hepatitis B virus", J. Vir. Hepatitis, vol. 16, No. 3, 2009, pp. 203-213 XP055389361.
Robles-Diaz M. et al., "Use of Hy's law and a new composite algorithm to predict acute liver failure in patients with drug-induced liver injury", Gastroenterology, vol. 147, No. 1, 2014, pp. 109-118 XP055387085.
Peta V. et al., "Serum apolipoprotein A1 and haptoglobin, in patients with suspected drug-induced liver injury (DILI) as biomarkers of recovery", PLOS ONE, vol. 12, No. 12, 2017; pp. 1-16 XP055469291.
Bell L. N. et al., "Serum proteomic profiling in patients with drug-induced liver injury", Aliment Pharmacol Ther., vol. 35, No. 5, 2012, pp. 1-22.
Borlak J. et al., "Serum acute phase reactants hallmark healthy individuals at risk for acetaminophen-induced liver injury", Genome Medicine, vol. 5, No. 86, 2013, pp. 1-14.
Church R. et al., "Candidate biomarkers for the diagnosis and prognosis of drug-induced liver injury: an international collaborative effort", Hepathology, pp. 1-43.
Shirani A. et al., "Therapeutic Advances and Future Prospects in Progressive Forms of Multiple Sclerosis", Neurotherapeutics, vol. 13, 2016, pp. 58-69.

*Primary Examiner* — Olga N Chernyshev
(74) *Attorney, Agent, or Firm* — POLSINELLI PC

(57) ABSTRACT

The present invention relates to new methods for assessing prognosis of recovery of DILI in a patient, combining measurement of serum markers through a logistic function that doesn't include bilirubin and transaminases (AST and ALT) markers.

2 Claims, 7 Drawing Sheets

|  | DILI n=154 | Not-DILI n=22 | Significance |
|---|---|---|---|
| Age | 52 (46-55) | 52 (36-58) | 0.62 |
| Gender female | 88 (57.1%) | 12 (54.6%) | 0.81 |
| BMI | 24.1 (23.4-24.8) | 25.9 (21.4-29.4) | 0.39 |
| *Drugs suspected* |  |  | *0.01* |
| Acetaminophen | 29 (18.8%) | 0 |  |
| Flupirtine | 14 (9.1%) | 0 |  |
| Methotrexate | 9 (5.8%) | 0 |  |
| Clavulanate | 8 (5.2%) | 0 |  |
| Isoniazid | 6 (3.9%) | 0 |  |
| Piperacillin | 6 (3.9%) | 0 |  |
| Other drugs | 82 (53.3%) | 22 (100%) |  |
| *Blood components* |  |  |  |
| ALT | 325 (244-414) | 349 (208-1035) | 0.87 |
| BILI | 21 (12-30) | 57 (14-242) | 0.04 |
| GGT | 217 (189-257) | 293 (121-495) | 0.25 |
| ApoA1 | 0.96 (0.82-1.11) | 0.74 (0.28-1.12) | 0.34 |
| HAPTO | 0.95 (0.76-1.10) | 0.93 (0.10-1.62) | 0.65 |
| A2M | 1.60 (1.56-1.71) | 1.75 (1.39-1.94) | 0.61 |
| AST | 147 (113-196) | 268 (106-643) | 0.16 |
| ActiTest | 0.93 (0.90-0.96) | 0.96 (0.83-0.99) | 0.64 |
| FibroTest | 0.54 (0.40-0.71) | 0.88 (0.45-0.97) | 0.08 |
| Mir-122 | 0.51 (0.08-1.20) | 0.03(-2.31-0.79) | 0.11 |

Figure 1

|  | APAP | Flupirtin | Methotrexate | Clavulanate | Isoniazid | Piperacillin | Others |
|---|---|---|---|---|---|---|---|
| Number cases | 29 | 14 | 9 | 8 | 6 | 6 | 82 |
| Age | 43 | 55 | 56 | 55 | 49 | 62 | 52 |
| Gender female | 19 (66%) | 13 (93%) | 6 (67%) | 3 (38%) | 3 (50%) | 0 (0%) | 43 (55%) |
| BMI | 23 | 26 | 30 | 24 | 19 | 24 | 24 |
| *Blood components* | | | | | | | |
| ALT (median) | 2727 | 449 | 178 | 147 | 536 | 451 | 284 |
| AST | 647 | 194 | 60 | 101 | 550 | 128 | 110 |
| BILI | 23 | 335 | 9 | 21 | 23 | 12 | 14 |
| GGT | 163 | 237 | 152 | 314 | 213 | 678 | 233 |
| ApoA1 | 0.95 | 0.27 | 1.38 | 0.88 | 0.49 | 0.94 | 1.14 |
| HAPTO | 0.89 | 0.10 | 1.15 | 1.40 | 1.27 | 1.78 | 1.02 |
| A2M | 1.45 | 1.70 | 1.67 | 1.60 | 1.96 | 1.40 | 1.67 |
| ActiTest | 1.00 | 0.98 | 0.82 | 0.81 | 0.97 | 0.94 | 0.91 |
| FibroTest | 0.39 | 0.99 | 0.30 | 0.58 | 0.66 | 0.61 | 0.50 |
| miR-122 | -0.07 | 0.48 | 2.12 | 1.14 | -0.26 | -0.52 | 0.80 |

Figure 2

| ALT cutoff | <132 IU/L (ULN= 66 IU/L) | | | <52 IU/L (ULN= 26 IU/L) | | |
|---|---|---|---|---|---|---|
| Recovery | No | Yes | P-value | No | Yes | P-value |
| N (% out of 115) | 37 (32%) | 78 (68%) | | 62 (54%) | 53 (46%) | |
| Age | 45 | 53 | 0.28 | 46 | 53 | 0.90 |
| Female (n=69) | 25 (36%) | 44 (64%) | 0.29 | 35 (56%) | 34 (44%) | 0.40 |
| Male (46) | 12 (26%) | 34 (74%) | | 27 (59%) | 19 (41%) | |
| BMI | 23 | 25 | 0.13 | 23 | 25 | 0.25 |
| *Drugs adjudicated* | | | *0.75* | | | *0.27* |
| Acetaminophen (18) | 7 (39%) | 11 (61%) | | 11 (61%) | 7 (39%) | |
| Flupirtin (12) | 4 (33%) | 8 (67%) | | 4 (33%) | 8 (67%) | |
| Methotrexate (9) | 1 (11%) | 8 (89%) | | 3 (33%) | 6 (67%) | |
| Clavulanate (6) | 2 (33%) | 4 (67%) | | 3 (50%) | 3 (50%) | |
| Isoniazid (4) | 2 (50%) | 2 (50%) | | 2 (50%) | 2 (50%) | |
| Piperacillin (4) | 2 (50%) | 2 (50%) | | 4 (100%) | 0 (0%) | |
| Other drugs (62) | 19 (31%) | 43 (69%) | | 35 (56%) | 27 (44%) | |
| *Blood components* | | | | | | |
| ALT (median) | 486 | 254 | 0.01 | 393 | 227 | 0.04 |
| BILI | 160 | 85 | 0.003 | 25 | 11 | 0.30 |
| GGT | 209 | 237 | 0.90 | 212 | 236 | 0.93 |
| ApoA1 | 0.53 | 1.14 | 0.01 | 0.96 | 1.02 | 0.50 |
| HAPTO | 0.82 | 1.09 | 0.04 | 0.92 | 1.10 | 0.67 |
| A2M | 1.66 | 1.61 | 0.77 | 1.60 | 1.70 | 0.30 |
| AST | 208 | 114 | 0.003 | 181 | 113 | 0.02 |
| ActiTest | 0.98 | 0.90 | 0.005 | 0.96 | 0.91 | 0.08 |
| FibroTest | 0.93 | 0.52 | 0.02 | 0.55 | 0.65 | 0.83 |
| Mir-122 | 0.03 | 0.81 | 0.12 | 0.06 | 1.20 | 0.01 |

Figure 3

|  | APAP | Flupirtin | Methotrexate | Clavulanate | Isoniazid | Others |
|---|---|---|---|---|---|---|
| Number cases | 10 | 10 | 8 | 4 | 3 | 46 |
| Age | 43 | 55 | 56 | 55 | 49 | 52 |
| Gender female | 6 (60%) | 9 (90%) | 6 (75%) | 3 (75%) | 3 (100%) | 43 (93%) |
| BMI | 23 | 26 | 30 | 24 | 18 | 23 |
| *Blood components* | | | | | | |
| ALT | 3459 | 641 | 165 | 168 | 1736 | 225 |
| AST | 835 | 236 | 59 | 88 | 1144 | 98 |
| BILI | 45 | 319 | 7 | 9 | 199 | 18 |
| GGT | | | | | | |
| ApoA1 | 0.91 | 0.34 | 1.41 | 0.97 | 0.39 | 1.10 |
| HAPTO | 0.64 | 0.10 | 1.18 | 2.02 | 0.10 | 0.99 |
| A2M | 1.51 | 1.70 | 1.63 | 1.68 | 1.62 | 1.88 |
| ActiTest | 1.00 | 0.99 | 0.73 | 0.81 | 1.00 | 0.88 |
| FibroTest | 0.65 | 0.99 | 0.22 | 0.58 | 0.95 | 0.67 |
| miR-122 | 0.69 | 0.29 | 2.39 | 0.77 | -0.58 | 1.29 |

Figure 4

|  | Flupirtin | Methotrexate | Clavulanate | Isoniazid | Piperacillin | Others |
| --- | --- | --- | --- | --- | --- | --- |
| APAP | BILI, HAPTO, ApoA1, FibroTest | ALT, AST, miR122, ActiTest | ALT, AST, ActiTest | None | GGT | ALT, AST, A2M, ActiTest |
| Flupirtin |  | BILI, HAPTO, ApoA1, FibroTest | HAPTO, FibroTest | None | HAPTO, FibroTest | BILI, HAPTO, ApoA1, FibroTest |
| Methotrexate |  |  | None | None | GGT | None |
| Clavulanate |  |  |  | None | None | None |
| Isoniazid |  |  |  |  | None | None |
| Piperacillin |  |  |  |  |  | None |

Figure 6

|         | Baseline | | Week 4-8 | | Week 8-12 | |
|---------|----------|-----|----------|-----|-----------|-----|
|         | BILI | ALT | BILI | ALT | BILI | ALT |
| ApoA1   | -0.86 (-0.91;-0.79)*** | -0.28 (-0.46;-0.06)* | -0.78 (-0.85;-0.68)*** | -0.28 (-0.47;-0.07)* | -0.64 (-0.88;-0.36)*** | -0.26 (-0.45;-0.04) |
| HAPTO   | -0.53 (-0.67;-0.36)**** | -0.22 (-0.42;-0.01) | -0.59 (-0.71;-0.43)**** | -0.19 (-0.39;0.03) | -0.73 (-0.82;-0.61)*** | -0.22 (-0.42;-0.00) |
| A2M     | -0.04 (-0.26;0.18) | -0.21 (-0.41;0.01) | -0.02 (-0.24;0.20) | 0.04 (-0.18;0.26) | 0.01 (-0.21;0.22) | -0.12 (-0.33;0.10) |
| GGT     | 0.10 (-0.13;0.31) | 0.16 (-0.06;0.38) | -0.05 (-0.26;0.17) | 0.32 (0.11;0.50)* | 0.25 (0.03;0.44) | 0.48 (0.30;0.63)*** |
| Mir-122 | -0.29 (-0.48;-0.07)** | -0.64 (-0.75;-0.49)*** | -0.24 (-0.44;-0.02) | -0.61 (-0.73;-0.45)*** | -0.11 (-0.32;0.11) | -0.31 (-0.50;-0.10)* |

Figure 7

METHOD OF DIAGNOSIS OF DRUG INDUCED LIVER INJURY

CROSS-REFERENCE TO RELATED APPLICATIONS

This application is a national stage application (under 35 U.S.C. § 371) of PCT/EP2018/055508, filed Mar. 6, 2018, which claims benefit of European Application No. 17305242.4, filed Mar. 7, 2017, which are incorporated herein by reference in their entireties.

The invention relates to a new non-invasive quantitative test making it possible to predict the outcome of Drug-Induced-Liver-Injury (DILI).

The liver is an organ that regulates the metabolism of internal compounds as well as external compounds such as drugs that are administered to a patient. Such drugs for therapeutic intent may cause serious or fatal liver injury in some patients, such injuries being unpredictable and possibly fatal to the patient.

Indeed, Drug-Induced-Liver-Injury (DILI) accounts for a little more than 10% of the cases of acute liver failure in the United States (Leise et al, Drug-Induced Liver Injury, Mayo Clinic Proceedings, Volume 89, Issue 1, January 2014, Pages 95-106,), with about one out of 50000 drug intake that can lead to acute liver failure and a fatal issue.

Multiple drugs may cause DILI, such as amoxicillin/clavulanate isoniazid, and nonsteroidal anti-inflammatory drugs which are among the most common causes of DILI.

Generally, stopping the drug intake would lead to improvement of the patient, although a high bilirubin value (higher than 3 g/dL) is associated with mortality of at least 10%.

As indicated by Leise et al (op. cit.) and by the FDA, there is a need to find and validate new biomarkers for DILI.

See Pauls and Senior, Mar. 20-21, 2013 Annual Meeting, co-sponsored by FDA/PhRMA, C-Path and AASLD or in the FDA Guidance for developing new drugs.

Preferably, these biomarkers should be able to predict the outcome of the liver disease when a patient presents some signs of liver failure, as soon as possible, in order to be able to stop the treatment before there are any fatal consequences thereof. Since DILI is patient-dependent (a drug may cause DILI in some patients and not in others)

It is also important to be able to evaluate the risk that a given drug will induce DILI (and acute liver failure) (i.e. estimate the prevalence of DILI associated with this drug), soon enough in the development process to be able to, either stop the development process at an early stage or closely monitor the patient's side effects, if the expected therapeutic advantages of the drug are higher than the drawbacks associated with DILI. It is also important, in case of DILI, to be able to determine if the patient is at risk of developing acute liver failure or recover.

A predictive test based on biomarkers should also be more precocious than dosage of the transaminases or of the bilirubin.

WO 2010/025410 provides methods and kits for identifying patients at risk of suffering from a drug induced liver injury, or for identifying patients who are suffering from early stages of a liver disorder by assessing the levels of apolipoprotein in a sample of the patient and comparing that to a reference value. The method may further comprise measuring at least one of a level of alanine aminotransferase (ALT) in the patient and a level of total bilirubin in the patient and comparing the measured level to a reference value of ALT or a reference level of total bilirubin in the population.

Poynard et al (2011, BMC GASTROENTEROLOGY, vol. 11, no. 1, 39) relates to the applicability and precautions of use of the FibroTest™, which is a validated test for detecting liver fibrosis. Fibrotest is comprised of a biomarker assays part where alpha2-macroglobulin (A2M), apolipoprotein A1 (ApoA1), haptoglobin, gamma-glutamyl-transpeptidase (GGT) and total bilirubin (bilirubin) are measured, as well as of a software part to obtain a score adjusted for age and gender. This document is not concerned with the detection of DILI events.

Munteanu et al (2016, Aliment Pharmacol Ther;44(8): 877-89) relates to the assessment of various tests, namely SteatoTest, ActiTest and FibroTest as non-invasive tests to determine whether they can be an alternative to biopsy in patients with NAFLD (non-alcoholic fatty liver disease). This document is not concerned with the detection of DILI events.

Poynard et al (2009, J. Vir. Hepatitis, vol. 16, no. 3, 203-213) aims at assessing the utility of FibroTest-ActiTest (FT-AT) as noninvasive markers of histological changes in patients with chronic hepatitis. The predictive value of FT-AT was assessed using the area under the receiver operating characteristics curves (AUROCs) for the diagnosis of bridging fibrosis, cirrhosis and moderate-severe necro-inflammatory activity. This document is not concerned with the detection of DILI events.

US 2011/256561 relates to detection of a liver condition by measuring the concentrations of γ-Glu-X (X represents an amino acid or an amine) peptides or the levels of AST or ALT in blood.

Robles-Diaz et al (2014, Gastroenterology. July;147(1): 109-118) relates to the determination of the risk for acute liver failure (ALF) in patients with DILI using the levels of bilirubin or transaminases (ALT, AST).

EP 1 311 857 B1 relates to method and test for detecting the extend of liver fibrosis, by using the serum concentration of biological markers. This document is not concerned with the detection of DILI events.

The test as described herein can be used to monitor DILI induced by various drugs that are known to have an increased risk of such effect.

One can cite acetaminophen (paracetamol), flupirtine, isoniazid, troglitazone, ximelegatran, leflunomide, nefazodone, nevirapine, pyrazinamide/rifampin, terbinafine, valproic acid, zifirlukast, atomoxetine, interferon 1b/1a, saquinavir, infliximab, trovofloxacin, bosentan, telithromycin, felbamate, erlotinib, natalizumab, tolcapone, bromfenac, pemoline, lumaricoxib, kava, lipokinetix.

Some other drugs may also lead to DILI, including phenytoin, sulfonamides, allopurinol, halothane, diclofenac, quinolones, telithromycin, INH, troglitazone, ximelagatran, bromfenac, estrogens, 17a androgens, chorpromazine, clavulinic acid, piroxicam, carbamazepine, chorpromazine, chlorpropramide, cyproheptadine, thiabendazole, haloperidol, valproate, tetracycline, didanosine, amiodarone, perhexiline maleate, dantrolene, methyldopa, nifurantoin, oxyphenisatin, propylthiouracil, and tienilic acid.

Table 2 of Bell et al ([16], Aliment Pharmacol Ther. 2012; 35(5): 600-612) also discloses a list of molecules and of associations of molecules that can induce DILI (abacavir/lamivudine, Allopurinol, alprazolam, amiodarone, Amiodarone, Amitriptyline, Amlodipine, Amoxicillin/clavulanate, ampicillin/, Anabolic steroid, Antithymocite, asparaginase, Atorvastatin, Atripla, Azathioprine, Azithromycin, bactrim, Bortezomib, Carbamazapine, Ceftriaxone, Chlorzoxazone, Ciprofloxacin, clindamycin, cyclophosphamide, Darunavir, Dicloxacillin, didanosine, diltiazem, Disulfiram, Drospirenone/ethinylestradiol, Duloxetine, fenofibrate, Fenofibrate, Flavocoxid, fluconazole, immunoglobulin, Isoflurane, Isoniazid, labetalol, Lamotrigine, levofloxacin, lisinopril, lorazepam, mercaptopurine, Metformin, Methyldopa, Metoprolol, metronidazole, Minocycline, Moxifloxacin, neomycin, nicotinic acid, Nitrofurantoin, Octreotide, orlistat, Oxacillin, phenobarbital, Phenylpropanolamine, Phenytoin, Phenytoin, Pregabalin, Rifabutin, rifampicin, rosiglitazone, Sertraline, simvastatin, Simvastatin, sulbactam fluconazole, Telithromycin, tetracycline, Trimethoprimsulfamethoxazole, Valaciclovir, valproic acid, Voriconazole, ziprasidone, Vincristine).

It is recognized in the art that severity of DILI can't be assessed merely by the level of serum enzyme elevation; although it may indicate the rate of hepatocellular injury, it doesn't measure the ability of the liver to function and support life. In other words, serum enzymes levels do not represent the state of liver function.

Consequently, although the signal currently considered most specific for and predictive of severe drug induced liver injury (DILI) is an elevation of total bilirubin (BILI) levels along with clinically relevant elevations of aminotransferase activities ("Hy's law"), sensitivity of this signal is inadequate to support early detection of injury as damage has already reached an extent where the function of the liver is compromised.

In summary, it is important to develop new tests that are able to respond to the following questions:

Does a given drug cause clinically significant DILI and, most importantly significant ALF, in the target treatment population?

Is it possible to determine ranges of dose & duration of exposure that are associated with an increased risk?

Is it possible to determine, for a given patient, whether there is an increased risk of developing ALF in case of DILI?

A test should be able to be used during the development phases of a new drug, as well as after approval of the drug.

Bell et al ([16], Aliment Pharmacol Ther. 2012; 35(5): 600-612) performed a serum proteomic profiling in patients with DILI. Multiple proteins were identified. However, although Bell et al suggests that the data reported may be helpful to better understand the mechanisms of DILI, they don't teach nor suggest to measure the values of markers in the blood, plasma or serum, or to combine them. Furthermore, the 9 priority 1 proteins, the expression of which was significantly different when comparing all three severity groups, don't comprise Apo-A1 or Haptoglobin (HAPTO).

Borlak et al ([13], Genome Medicine 2013, 5:86) evaluate serum acute phase reactants linked to acetaminophen-induced liver injury. The study is thus limited to specific type of DILI (induced by a specific drug). The authors don't discuss the severity or prognosis of DILI, and the data reported therein is different, with regards to haptoglobin to the one reported here.

The present application discloses a new test that makes it possible to obtain and evaluate the prognosis of the outcome of Drug-Induced-Liver-Injury (DILI) in a patient (i.e. to determine the risk of a patient to develop acute liver failure after being administered with a given substance/composition, and thus to monitor for a possible risk of progression drug related liver injury to severe DILI, or the prognosis that the patient will fully recover, as defined below) comprising the step of combining the values as measured from markers present in the blood, serum or plasma of said patient through a logistic function This method is performed in vitro, or ex vivo.

This method is particularly interesting in that it makes it possible to evaluate this prognosis even for patients for which no liver information history is available (i.e. the patients for which the values of the biochemical markers used in the logistic function are not known before the DILI arises in the patient).

Among the markers that are used in the logistic function, one shall not include the level of bilirubin (total bilirubin) an/or the level of ALT (alanine aminotransferase) or AST (Aspartate Aminotransferase).

A contrario, it is preferred when the function uses the levels of Haptoglobin and of Apolipoprotein A-I (apoA1).

The present test is particularly adapted for patients suspected of presenting acute DILI. These patients would present the following criteria:

a) ALT activity exceeding 3× ULN (upper limit of normal) or ALP (Alkaline phosphatase) >2× ULN, within 4 weeks before the inclusion visit (D0);

b) an increase of at least 2-fold the pre-treatment level to D0 was required when pre-treatment ALT or ALP activity was available and >ULN;

c) a history of drug intake, including any prescription drugs, over-the-counter drugs, recreational drugs (e.g. cocaine, ecstasy, amphetamines), herbal medications or food supplements in the 6-12 months prior to the DILI onset;

d) absence of other known causes of liver injury.

The ULN (upper limit of normal) is a value that it widely used in the art.

One can take, as the ULN for ALP, 160 U/L.

As there is wide variability in the definition of the ULN for ALT, two previously published definitions can be used: one set at 26 IU/L or the other set at 66 IU/L.

For bilirubin, ULN is defined as 17 μmol/l., so that 2× ULN=34 μmol/l.

The method may not be suitable for patients who present any other likely alternative cause for the liver injury, such as acute or chronic viral hepatitis (including HVE), or those detailed in the protocol, the most frequent being chronic autoimmune liver disease, primary biliary cirrhosis (PBC), primary sclerosing cholangitis (PSC), extra-hepatic cholestasis, ischemic liver damage and the presence of liver metastasis or other malignant diseases.

Full recovery was defined as an ALT <2× ULN and BILI <2× ULN attained between 8 and 12 weeks. The method herein disclosed thus makes it possible to determine whether the patient will attain recovery or whether the acute DILI would lead to the need of liver transplant or risk of death of the patient.

The invention thus relates to an in vitro (or ex vivo) method for prognosis of the outcome of Drug-Induced-Liver-Injury (DILI) in a patient (i.e. determine the risk of a patient to develop acute liver failure, monitoring for a possible risk of progression drug related liver injury to severe DILI, and/or determine whether the patient will recover from DILI) comprising the step of combining the values as measured from markers present in the serum or plasma of said patient through a logistic function, wherein the logistic function doesn't use the value of bilirubin and/or of transaminases (ALT or AST).

In a preferred embodiment, these markers are selected from the group consisting of α2-macroglobulin, GGT (gammaglutamyl transpeptidase), haptoglobin, Apolipoprotein A-I (apoA1), triglycerides, total cholesterol, fasting glucose, γ-globulin, albumin, α1-globulin, α2-globulin, β-globulin, IL10, TGF-β1, apoA2, apoB, cytokeratin 18, platelets number, prothrombin level, hyaluronic acid, urea, N-terminal of type III pro-collagen, Tissue inhibitor metalloproteinase type-1 (TIMP-1), type IV collagen (Coll IV), osteoprotegerin, miRNA122, cytokeratin ck18, SAA (serum amyloid A), alpha-1-antitrypsin (isoform 1), Fructose-bisphosphate aldolase A, Fructose-bisphosphate aldolase B, Fumarylacetoacetase, Transthyretin, PR02275, C-reactive protein (isoform 1), Leucine-rich alpha-2-glycoprotein, Serpin A11, DNA-directed RNA polymerase I subunit RPA1, Obscurin (isoform 1), alpha-skeletal muscle actin, Aortic smooth muscle actin, Alkaline Phosphatase, Uncharacterized protein C22orf30 (isoform 4), Serum amyloid A2 (isoform a), Apolipoprotein C-III, Apolipoprotein E, Apolipoprotein A-II, Polymeric immunoglobulin receptor, von Willebrand factor, Aminoacylase-1, G-protein coupled receptor 98 (isoform 1), Paraoxonase/arylesterase 1, Complement component C7, Hemopexin, Complement C1q subcomponent, Paraoxonase/lactonase 3, Complement C2 (fragment), Versican core protein (isoform Vint), Extracellular matrix protein 1 (isoform 1), E3 SUMO-protein ligase RanBP2, Haptoglobin-related protein (isoform 1), Adiponectin, Retinol Binding Protein, Ceruloplasmin, Alpha 2 antiplasmin, Antithrombin, thyroxin binding protein, Protein C, alpha 2lipoprotein and Tetranectin.

In the context of the method herein disclosed, the logistic function would preferably combine at least 3, more preferably at least 4 markers as disclosed above.

The method herein disclosed thus makes use of an ex vivo combination of the results calculated using values as previously measured, through a logistic function, in order to obtain an end-result that is indicative of the prognosis of evolution of DILI. it would thus exclude any step applied on the human body of the patient. In the method herein disclosed, it is understood that the markers are circulating proteins or natural elements that are present in the blood, plasma or serum of a patient. The values of the chosen markers shall be measured on a sample of blood, plasma or serum previously harvested, according to methods known in the art. The values are expressed in the units according to the art. However, should other units be chosen by the person skilled in the art to expressed the measured values, this would only change the coefficients within the logistic function. The method would thus still be applicable.

In the preferred embodiment, the method as herein disclosed makes use of a logistic function that includes the values measured for haptoglobin and ApoA1.

As will be discussed below, it has been noticed that the kinetics of variation of the concentration of haptoglobin and ApoA1 are different from these of transaminases. It is thus of particular interest to include these two markers within the logistic function. It is further demonstrated that their inclusion will make it possible to increase the sensitivity of the logistic function, which may broaden its usability, in particular by improving the prognosis of outcome of DILI for more types of drugs such as flupirtine.

In a specific embodiment, the logistic function includes the values measured for ApoA1, A2M (α2-macroglobulin), GGT and Haptoglobin. In a more specific embodiment, the logistic function doesn't include the values of other markers of blood, serum or plasma. In other words, the only values of blood, serum or plasma markers that are used within the logistic function are the values measured for ApoA1, A2M (α2-macroglobulin), GGT and Haptoglobin.

The logistic function may further include at least one other variable chosen in the group consisting of gender, age and BMI of the patient. In this embodiment, the logistic function will use both the values of the markers from blood, serum or plasma and the value measured from at least one of the other variable as recited above. It is preferred when the logistic function further takes into consideration both the gender (sex) and the age of the patient.

In this specific embodiment, the logistic function is a1+a2×Age (years)+a3×ApoA1 (g/l)+a4×Log (A2M, g/l)+a5×Log(GGT, IU/l)+a6×Log (Hapto, g/l)+a7×Gender (0 for women, 1 for men).

The coefficients are calculated as disclosed below, and they are generally as follows:
  i. $0.5 \leq a1 \leq 0.8$ preferably $0.55 \leq a1 \leq 0.65$
  ii. $0.02 \leq a2 \leq 0.04$ preferably $0.02 \leq a2 \leq 0.03$
  iii. $1.1 \leq a3 \leq 1.3$ preferably $1.15 \leq a3 \leq 1.25$
  iv. $-1.4 \leq a4 -1.2$ preferably $-1.35 \leq a4 \leq -1.25$
  v. $-1.1 \leq a5 \leq -0.9$ preferably $-1.05 \leq a5 \leq -0.95$
  vi. $0.1 \leq a6 \leq 0.3$ preferably $0.2 \leq a6 \leq 0.3$
  vii. $-0.55 \leq a7 \leq -0.35$ preferably $-0.5 \leq a7 \leq -0.4$.

In a preferred embodiment, the logistic function is 0.605+0.027×Age (years)+1.197×ApoA1 (g/L)−1.31×LogA2m (g/L)−1.011×LogGGT (IU/L)+0.24 ×LogHaptoC (g/L)−0.44×Sex (0 for women, 1 for men).

When this function is used, a result below 0.25 would indicate that the patient will recover from DILI, whereas a result above 0.75 would indicate that DILI is likely to evolve to Acute Liver Failure. When the result is between 0.25 and 0.75 the physician would evaluate other parameters to determine whether the patient is likely to recover from the DILI or whether there is a risk that it would worsen toward liver failure.

The method and the function as herein disclosed may be used to determine the individual risk of a patient to develop liver failure in response to a given substance or composition. It is usually used when the patient already present DILI.

It could also be used when a treatment involving a substance that is known to be at risk of inducing DILI is used for a patient. Indeed, evolution of the end value of the logistic function would provide some information to the physician as to the risk of developing DILI and also liver failure.

The method and function as herein disclosed may also be used to characterize whether a specific drug is at risk of inducing DILI. The risk may be compared to the risk of a known positive control (substance that is known to induce DILI), using the method and logistic function as disclosed herein.

The method may be of particular advantage and interest in the process of development of a new drug or medicament, during clinical trials, as it is important to evaluate and document the DILI risk for new pharmaceutical products.

One can thus perform a method to determine whether a given substance of interest presents a per se risk to induce acute liver failure. This method would comprise the step of performing the method as disclosed above (combining the values of biochemical markers and potentially other variables in a logistic function as herein disclosed) for various patients of a cohort.

The study is performed on a cohort of patients. In fact, one should perform the study on a number of patient high enough to obtain statistically relevant results for the molecule that one desires to test (substance or drug of interest), and eliminate the inter-patients variability.

The substance of interest will preferably be compared to a placebo, i.e. a molecule that is known not to induce DILI.

Advantageously, one can also use positive controls, i.e. drugs that are known to induce DILI. These positive controls should be used under strict control.

Different positive controls could be used, as the data reported below show that DILI induced by acetaminophen and flupirtine may not involve the same mechanisms. As the positive control one can use any drug as indicated above. It is however, preferred to use a positive control that is well known and that would be adapted to the patient receiving this control. Acetaminophen may thus be particularly adapted as the positive control.

The study is performed on a patient cohort, according to a protocole that could the as follows, for each patient:
- The end result of the logistic function as herein disclosed is calculated before the patient receives the substance to be tested
- The end result of the logistic function is calculated after the patient receives the substance to be tested (which can thus be the substance of interest, the placebo or the positive control)

It may be preferred to calculate the end result of the logistic function at different times over a given period (such as a few days), in order to evaluate the evolution of such end result overtime.

The above steps are performed for each patient of a cohort of patients, and the end value of the logistic function is thus obtained for each patient and for the different tested substances.

For each moment at which the end result has been calculated, one would calculate the mean of the different values for each patient and for each substance (substance of interest, and potentially placebo and positive control(s)), in order to remove the inter-patient variability (i.e. the fact that two patients may react differently to a given substance or medicament).

The mean of the end results is a value that would take into consideration the per se potential of the substance to induce DILI.

It is preferred when the cohort of patients (the number of patients on which the substance of interest will be tested) contains at least 10 patients, preferably at least 20 patients, or more preferably at least 50 patients. The person skilled in the art will determine the adequate number of patients in order to obtain results that are statistically significant.

It is also preferred when pharmacokinetics and dose responses studies have been made before these studies are performed beforehand in order to calculate the various end result at the best times depending of the in vivo behavior of the substance of interest.

It is possible to have multiple sub-cohorts, with patients of one sub-cohort receiving the substance of interest to be tested, patients of another sub-cohort receiving the placebo and patients of one (or more) sub-cohort(s) receiving the positive control.

The determination of the potential of a substance of interest to induce DILI, one would be different, depending on whether controls were used or not.

When a positive control has been used:
The end value for the logistic function is calculated for each patient, receiving the placebo, the positive control and/or the substance of interest, and means are calculated for each time point determined by the physician, according to the phamarcokinetics of the test molecule.

If the mean (or the median) obtained for the substance of interest is significantly higher than the one obtained for the positive control, this molecule has a risk of inducing DILI which the more important as the mean is higher.

If the mean (or the median) obtained for the substance of interest is equal or significantly lower than the one obtained for the placebo, one could conclude that this molecule has no real risk of inducing DILI in the conditions of use.

If the mean (or the median) obtained for the substance of interest is significantly higher than the one obtained for the placebo but lower than the one of the positive control, further studies may be needed.

If no positive control has been used, the logistic function may also be used, with a placebo.

The means obtained for each time points for the substance of interest and the placebo are compared.

If the mean for the substance of interest is not significantly different or significantly lower than the mean for the placebo, the molecule (substance of interest) can be considered as without risk of inducing DILI.

If the mean for the substance of interest is significantly higher than the mean for the placebo, the molecule (substance of interest) would need further investigations as to its risk of inducing DILI.

The method can be performed when some patients of the cohort are administered the substance of interest wherein other patients of the cohort are given a placebo that is known not to induce DILI (or ALF). In this embodiment, the end results obtained from the logistic function are compared between the placebo and the given substance group (generally the means or medians).

As indicated, in another embodiment, some patients of the cohort are administered the given substance of interest and other patients of the cohort are given a control substance that is known to be at risk of inducing DILI (or ALF). In this embodiment, the end results obtained from the logistic function are compared between the control substance and the given substance groups.

The invention also relates to a device for prognosis the outcome of Drug-Induced-Liver-Injury (DILI) in a patient, comprising a first means, wherein the first means provides a index by combining the values as measured from markers present in the serum or plasma of a patient through a logistic function.

The logistic function, and markers to be implemented within this device are the ones disclosed in the present specification. Consequently, the markers don't include bilirubin and transaminases, and preferably include haptoglobin and/or ApoA-1.

As herein disclosed the device preferably makes it possible to obtain the index using the following logistic function: $0.605 + 0.027 \times \text{Age (years)} + 1.197 \times \text{ApoA1 (g/L)} - 1.31 \times \text{LogA2m (g/L)} - 1.011 \times \text{LogGGT (IU/L)} + 0.24 \times \text{LogHaptoC (g/L)} - 0.44 \times \text{Sex}$ (0 for women, 1 for men).

The invention also comprise the step of performing a Fibrotest® after applying the logistic function as disclosed above.

The Fibrotest® combines five markers: alpha2-macroglobulin, haptoglobin, apolipoprotein A2, total bilirubin and gamma-glutamyl transpeptidase (GGT), and adjusts with sex and age. The algorithm for Fibrotest® reads as follows: $4.467 \times \text{Log(Alpha2Macroglobulin (g/l))} - 1.357 \times \text{Log(Haptoglobin (g/l))} + 1.017 \times \text{Log(GGT (IU/l))} + 0.0281 \times \text{Age (in years)} + 1.737 \times \text{Log(Bilirubin (µmol/l))} - 1.184 \times \text{ApoA1 (g/l)} + 0.301 \times \text{Sex (female=0, male=1)} - 5.540$. It is performed in vitro on a biological sample (blood or serum) that has been harvested from a patient.

Although the present application discloses a logistic function that can be used in the methods herein proposed, the present invention also relates to a method for obtaining a logistic function that can assist a physician to determine whether a patient is at risk of ALF wherein said logistic function combines the values of the concentration of biochemical markers in the serum of said patient. Thus, depending on the markers that are chosen by the person skilled in the art, other logistic functions can be obtained.

The art already describes different means making it possible to obtain a logistic function, the end value of which is indicative of the degree of liver fibrosis. In particular, one can cite WO 2002/016949, and different declinations of the method first described in WO 2002/016949: WO 2010/149767, WO 2006/10357, WO 2006/082522, WO 2003/073822, WO 2011/039321, WO 2005/116901, WO 2010/058295, WO 2010/097472.

In the present case, the end value of the logistic function obtained by the method disclosed below is indicative of the ability for the patient to recover from DILI.

The method to obtain such a logistic function shall comprise the steps of:
a) assessing the recovery from DILI at 12 weeks for patients having DILI, wherein recovery of DILI is defined as ALT <132 IU/L, and BILI <2× ULN
b) identifying, among the biochemical markers, the value of which has been measured, the ones which differ significantly, between groups of
  i. the patients having recovered and
  ii. the patients that didn't recover, by unidimensional analysis
c) performing a logistic regression analysis to assess the independent discriminative value of these markers identified in step b) for the prognosis of recovery of DILI at 12 weeks
d) obtaining the logistic function by combination of these identified independent factors,
wherein the markers of step b) do not include total bilirubin and/or ALT (alanine aminotransferase).

In a particular the biochemical markers the value of which is used for obtaining the logistic function are selected from the group consisting of α2-macroglobulin, GGT (gamma-glutamyl transpeptidase), haptoglobin, apoA1, triglycerides, total cholesterol, fasting glucose, γ-globulin, albumin, α1-globulin, α2-globulin, β-globulin, IL10, TGF-β1, apoA2, apoB, cytokeratin 18, platelets number, prothrombin level, hyaluronic acid, urea, N-terminal of type III procollagen, Tissue inhibitor metalloproteinase type-1 (TIMP-1), type IV collagen (Coll IV) osteoprotegerin, miRNA122, cytokeratin ck18, SAA (serum amyloid A), alpha-1-antitrypsin (isoform 1), Fructose-bisphosphate aldolase A, Fructose-bisphosphate aldolase B, Fumarylacetoacetase, Transthyretin, PR02275, C-reactive protein (isoform 1), Leucine-rich alpha-2-glycoprotein, Serpin A11, DNA-directed RNA polymerase I subunit RPA1, Obscurin (isoform 1), alpha-skeletal muscle actin, Aortic smooth muscle actin, Alkaline Phosphatase, Uncharacterized protein C22orf30 (isoform 4), Serum amyloid A2 (isoform a), Apolipoprotein C-III, Apolipoprotein E, Apolipoprotein A-II, Polymeric immunoglobulin receptor, von Willebrand factor, Aminoacylase-1, G-protein coupled receptor 98 (isoform 1), Paraoxonase/arylesterase 1, Complement component C7, Hemopexin, Complement C1q subcomponent, Paraoxonase/lactonase 3, Complement C2 (fragment), Versican core protein (isoform Vint), Extracellular matrix protein 1 (isoform 1), E3 SUMO-protein ligase RanBP2, Haptoglobin-related protein (isoform 1), Adiponectin, Retinol Binding Protein, Ceruloplasmin, Alpha 2 antiplasmin, Antithrombin, thyroxin binding protein, Protein C, alpha 2lipoprotein and Tetranectin.

In another embodiment, one shall also use at least one other variable selected from the group consisting of gender, age and BMI of the patient, in the logistic function as calculated in step d). These will be included in steps b) and c).

In another embodiment, though, the invention relates to a method for prognosis of the outcome of Drug-Induced-Liver-Injury (DILI) in a patient, comprising the step of harvesting blood, plasma or serum from a patient, measuring the value of markers present in the harvested sample and combining the values as measured through a logistic function as disclosed above. The markers are as disclosed above.

The following examples are meant to describe an aspect of invention, but shall not be limiting the invention.

DESCRIPTION OF THE FIGURES

FIG. 1: Characteristics of patients adjudicated as DILI or not, among the population suspected cases, the context of use population (n=176)

FIG. 2: Baseline characteristics of DILI cases (n=154) according to the drug. There was no significant difference between medians of age, and between gender's prevalence. There was a significant difference for BMI between Isoniazid and methotrexate.

FIG. 3: Prediction of recovery at inclusion, in adjudicated DILI cases (n=115)

FIG. 4: Baseline characteristics of DILI cases with 3 samples (n=81) according to the drug. There was no significant difference between medians of age, and between gender's prevalence. There was a significant difference for BMI between Isoniazid and methotrexate.

FIG. 6: Summary of significant (Bonferroni) differences of baseline test medians according to drugs, n=154. The drugs ranked according to the highest number of tests significantly different between the 6 others, were the following: APAP (n=16), flupirtin (n=16), methotrexate (n=9), Others (n=8), clavulanate (n=5), piperacillin (=4), and isoniazid (n=0). The tests ranked according to their highest number of significant differences between the 7 drugs, were the following: HAPTO (n=5), FibroTest (n=5), BILI (n=3), ALT (n=3), AST (n=3), ApoA1 (n=3), ActiTest (n=3), GGT (n=2), and miR122 (n=1). The tests with the same significant differences between drugs were the following: ALT, AST and ActiTest. ApoA1 was always associated with the BILI and HAPTO significant differences observed between flupirtin, methotrexate and Others. These 3 test were in the normal range in cases with methotrexate and Others, and dramatically abnormal (high BILI, low HAPTO and low ApoA1) in flupirtin cases.

FIG. 7: Correlation (Pearson) between ApoA1, HAPTO, A2M, GGT and Mir-122 with DILI references tests (BILI and ALT) at baseline, 4-8 weeks and 8-12 weeks (n=81). *P<0.0001 P<0.001 *P<0.01. According to the number of comparisons P value>0.01 were not considered as significant.

EXAMPLES

Example 1. Methods

Figure 5:
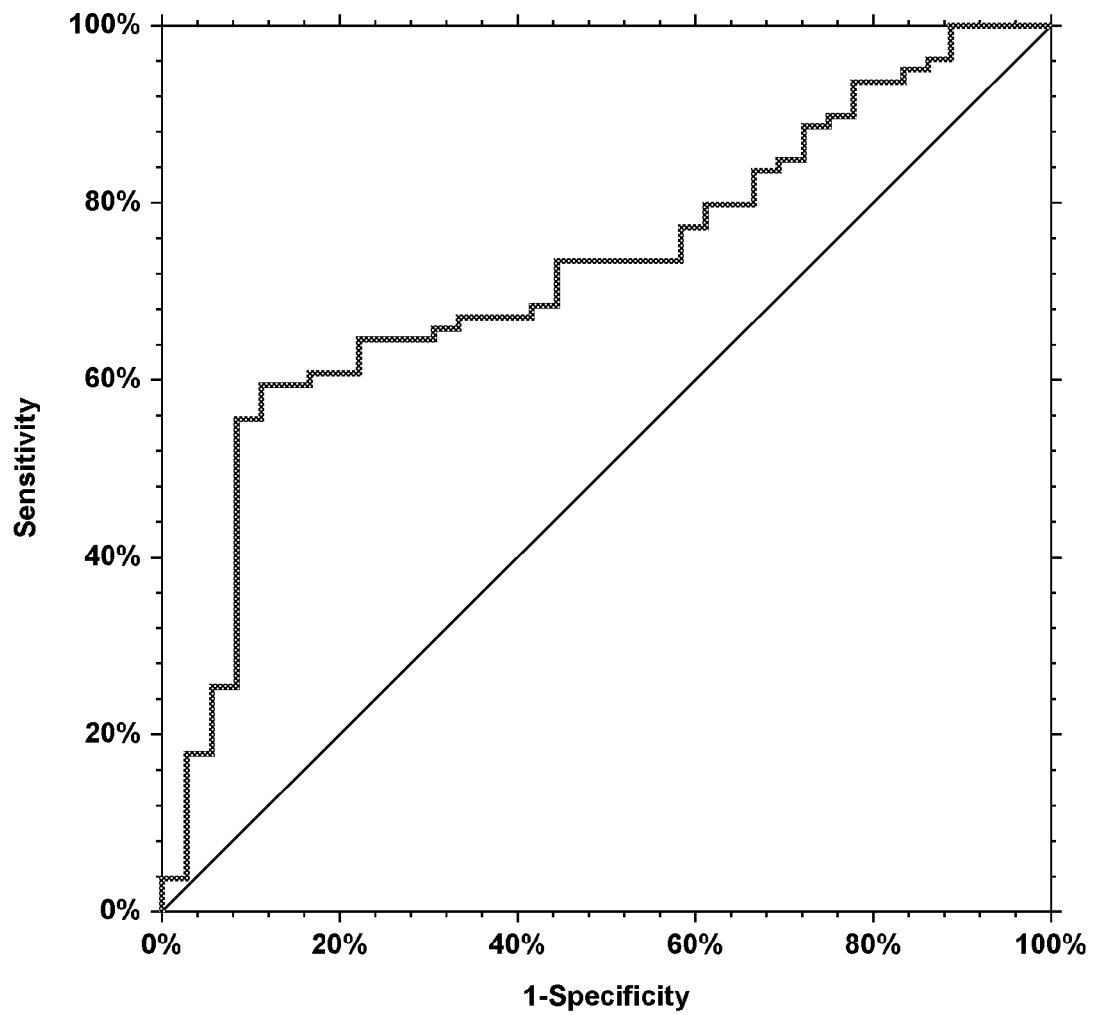
FIG. 5: AUROC of ActiTest-DILI. A multivariate regression analysis combining the ActiTest components without BILI and ALT, that is HAPTO, ApoA1, GGT, A2M, age and gender permitted a significant prediction of recovery, with accuracy=67.0% (77/115) and an AUROC=0.724 (P<0.001 vs no prediction 0.500).

The primary objective of the experiments herein disclosed was to analyze the performance of ActiTest and its components as predictors of the full recovery outcome after inpatient admission with DILI.

The ActiTest is calculated using an original combination of six highly concentrated biochemical markers, which are easy to assess. The ActiTest offers a non invasive alternative for measuring necro inflammatory activity in patients with chronic hepatitis C or B. The ActiTest combines alpha2-macroglobulin, haptoglobin, apolipoprotein A1, total bilirubin, GGT, and ALT, parameters adjusted for patient's age and gender. It is disclosed in EP 1311857.

Full recovery was defined as an ALT <2× the upper limit of normal (ULN), and BILI <2× ULN. As there is wide variability in the definition of the ULN for ALT, we used two previously published definitions in order to test the robustness of the biomarkers' performance: one set at 26 IU/L (i.e., 52 IU/L being 2× ULN for the recovery cutoff), and the other set at 66 IU/L (i.e., 132 IU/L being 2× ULN for the recovery cutoff) [11].

The second objective was to assess the possible benefits of the ActiTest components as markers of a specific drug signature, at inclusion or during follow-up. microRNA miR-122-5p (miRNA-122) was used as a marker of liver specificity.

According to the adjudication committee, when more than five cases had been reviewed, cases were classified into one of seven groups based on the responsible drug. These groups were acetaminophen (APAP, n=29), flupirtine (n=14), methotrexate (n=9) amoxicillin-clavulanate (n=8), isoniazid (n=6), piperacillin-tazobactam (n=6) and an "others" group with five or fewer cases (n=82).

In the study 10 tests (six components of ActiTest™, AST, miR-122, ActiTest and FibroTest) were compared according to the different groups of drugs.

The third objective was to assess at 8-12 weeks whether the serum values of ApoA1 and HAPTO, which should normally have returned to their baseline value prior to the DILI episode, remained elevated compared with patients without recovery. These two proteins were identified as being differentially expressed in DILI responders prior to APAP treatment [13]. Therefore, individuals with higher ApoA1 and HAPTO, could be at lower risk for DILI prior to drug treatment.

Another goal was to analyze the risk of fibrosis after DILI, using FibroTest™ and transient elastography (TE) performed after the acute phase of DILI [14].

Inclusion Criteria

All consecutive patients with suspected acute DILI were included if they met the following criteria: a) ALT activity exceeding 3× ULN or ALP >2× ULN, within 4 weeks before the inclusion visit (D0); b) an increase of at least 2-fold the pre-treatment level to D0 was required when pre-treatment ALT or ALP activity was available and >ULN; c) a history of drug intake, including any prescription drugs, over-the-counter drugs, recreational drugs (e.g. cocaine, ecstasy, amphetamines), herbal medications or food supplements in the 6-12 months prior to the DILI onset; d) absence of other known causes of liver injury; and e) patients aged >18 years who were capable of and willing to provide written informed consent.

Criteria for Exclusion

A main exclusion criteria was the presence of any other likely alternative cause for the liver injury, such as acute or chronic viral hepatitis (including HVE), or those detailed in the protocol, the most frequent being chronic autoimmune liver disease, primary biliary cirrhosis (PBC), primary sclerosing cholangitis (PSC), extra-hepatic cholestasis, ischemic liver damage and the presence of liver metastasis or other malignant diseases.

The adjudication committee had the final decision about the diagnosis of DILI and the drug presumed to be the main cause of DILI in cases involving co-prescriptions.

All cases were classified as hepatocellular, cholestatic or mixed, according to the initial serum ALT to alkaline phosphatase ratio (R ratio), both expressed as multiples of the upper limit of normal and rated according to the RUCAM score.

Endpoints

Full recovery was defined as an ALT <2× ULN and BILI <2× ULN attained between 8 and 12 weeks.

Biochemical Analyses

Measures of biochemical markers were performed accordingly to the art, and analyses of ActiTest® and FibroTest® were made as described in the art and in WO 2002/016949.

Total RNA, including miRNA was extracted from 200 µl of serum, using a commercial column-based system (Exiqon, Denmark) following the manufacturer's instructions. RNA synthetic control templates (Exiqon, Denmark) were introduced to provide controls for the quality of the RNA isolation. Serum levels of miR-122 and nine endogenous miRNAs as potential candidates for reference miRNAs were assayed using the Locked Nucleic Acid (LNA™)-based miRNA relative quantitative PCR with a SYBR® Green detection. cDNA synthesis and real time PCR were performed using the miRCURY LNA™ Universal RT cDNA Synthesis Kit (Exiqon, Denmark) and miRCURY LNA™ Universal RT microRNA PCR system (Exiqon), respectively. Two additional RNA spike-ins were also introduced to provide controls for the cDNA synthesis reaction and the PCR. Quantitative PCR was done on the LightCycler® 480 (Roche Applied Science) according to the manufacturer's instructions. The amplification curves were analyzed using the Roche LC software, both for the determination of cycle threshold (Ct) and for melting curve analysis. Ct values were then processed using the analysis software GenEx® (MultiD Analysis AB). Using both tools GeNorm® and NormFinder® incorporated in the GenEx® software, we identified miR-23a-3p as the most stable endogenous miRNAs in our study. Ct values for miR-122 were normalized with Ct value of miR-23a-3p. Levels of serum miR-122 were expressed in relative quantities calculated by the equation $2^{-\Delta Ct}$.

Statistical Methods

Comparisons between medians (95% confidence interval [CI]) used the Mann-Whitney test with Bonferroni correction, and the Tukey-Kramer multiple comparison procedure for analyses of variance of the three repeated measures. Correlation between test values was estimated using the Pearson coefficient, expressed with a 95% CI; according to the number of comparisons, only a P value <0.01 was considered significant. NCSS-9 software was used [15].

Example 2. Characterization of ApoA1 and HAPTO as Biomarkers of DILI Risk

ApoA1 and HAPTO (haptoglobin) in the 81 DILI cases remained significantly higher in the cases that recovered (n=65) versus those that did not (n=16) at inclusion, at 4-8 weeks and at 8-12 weeks.

The median values at 8-12 weeks in cases that recovered were in the range of normal values for ApoA1 (1.56 g/L [95% CI 1.49-1.68]) and for HAPTO (1.07 g/L [0.83-1.22]). The same results were observed after stratification on APAP cases and non-APAP cases.

Example 3. Risk of Fibrosis as Sequelae of DILI

FibroTest was not validated as a marker of fibrosis in acute liver disease and is not interpretable in chronic liver diseases with presumed high necroinflammatory histological activity defined as an ALT >622 IU/L [14].

The 81 cases with repeated measurements assessed the percentage of cases at very high risk of false positive of FibroTest in DILI.

At inclusion, 24 of the 81 cases (30.0%; 95% CI 20.0-40.8) had an ALT >622; 6 of the 81 (7.4%; 1.8 -15.4) at 4-8 weeks; and none of the 81 (0%; 0.0-4.5) at 8-12 weeks.

Three cases with ALT <622 IU/L at inclusion but with FibroTest outlier components were also uninterpretable at inclusion and at 4-8 weeks, but became interpretable at 8-12 weeks.

Therefore, these results strongly suggested not prescribing or interpreting FibroTest to assess fibrosis stage within 12 weeks of a DILI episode.

A total of 18 of 81 cases (22.2%; 13.7-32.8) still had a FibroTest >0.48 (median 0.70, range 0.482-0.997) at 8-12 weeks and therefore were presumed to be at risk of significant fibrosis (stage F2 to F4).

Only two of these cases were prospectively followed, and persistent intermediate fibrosis was suspected as presumed by FibroTest: 0.53 (F2) to 0.47 (F1) one month later for one APAP case, and 0.51 to 0.52 (still F2) estimated 877 days later for the second case that was initially treated by methotrexate.

These two cases had full recovery (BILI and ALT) at 8-12 weeks. They had no previous history of liver disease, but NAFLD was possible as the BMIs were 29 and 55 kg/m$^2$, respectively.

A total of 8 cases were followed with 3 measurements of TE concomitantly with FibroTest. Six out of the 8 cases (75%; 35-97%) were still considered to be false positives at 8-12 weeks (recovery as ALT <132 IU/L and TE >7.1 kPa) versus none of the 8 (0%; 0-37%; P=0.05) as presumed by FibroTest (<0.48).

Example 4. Prediction of Recovery

A total of 176 patients with acute liver injury (ALI) and suspected DILI, the "context of use population", and at least one sample available from the SAFE-T biobank and the GHPS biobank were included. After adjudication, 154 patients were considered to have DILI and 22 were considered to have ALI without DILI (FIGS. 1 and 2). A total of 115 DILI cases had at least two samples and follow-up, which enabled the recovery status to be assessed at 12 weeks (FIG. 3). A total of 81 DILI cases had three repeated measurements of the 10 tests, enabling a comparison of their 12-week dynamics (DYN-population) (FIG. 4). There were no significant statistical differences between the main characteristics of the different subpopulations, except that the 10 most frequent drugs in DILI were not observed in the ALI population, and two centers had more ALI patients than the others.

Using the same definition of recovery (<2 ULN for both ALT and BILI), a change in the definition of the ALT ULN "artificially" changed the prevalence of recovery from 53/115 (46.1%; 95% CI 36.8-56.1) to 78/115 (67.8%; 58.5-76.2; P=0.0009).

Using the more sensitive definition of recovery in the DILI cases (8-12 W ALT <132 IU/L), two components of ActiTest other than ALT and BILI, which had been used in the recovery definition, were predictive of recovery: high ApoA1 (P=0.01) and high HAPTO (P=0.04). Mir122 was associated with recovery (P=0.01) only when using the most specific cutoff (8-12 W ALT <52 IU/L). Using a multivariate regression analysis (combining the ActiTest components without BILI and ALT (used as references), i.e., HAPTO, ApoA1, GGT, A2M, age and gender, resulted in a significant prediction of recovery with 67.0% accuracy (77/115) and an AUROC of 0.724 (P<0.001 vs. no prediction 0.500) (FIG. 5). The formula used is 0.605+0.027×Age (years)+1.197× ApoA1 (g/L)−1.31×LogA2m (g/L)−1.011×LogGGT (IU/L)+0.24×LogHaptoC (g/L)−0.44×Sex (0 for women, 1 for men).

Example 5. Signatures of Tests According to Drugs at Inclusion

Six drugs had more than 5 cases and could be analyzed specifically; the other drugs remained in the mixed group named "others". Two drugs, APAP and flupirtine, clearly had more test signatures, each with 16 significant differences versus 9 for methotrexate, 5 for clavulanate, 4 for piperacillin, and no significant signatures for isoniazid.

After taking into account the number of comparisons, there were several significant differences in the test medians between drugs (FIG. 6).

When compared with most of the other classes of drugs, the flupirtine cases had the lowest ApoA1 (median 0.27 g/L) and HAPTO (0.10 g/L), and the highest BILI (335 µmol/L) and FibroTest (0.99).

There were four cases of DILI due to gabapentin/pregabalin, which are similar to flupirtine and its deaza analog retigabine, both in the pharmacological class of gamma aminobutyric acid (GABA) precursors/analogs. Several DILI cases with cross reactivation have been also published [15,16,17]. The four gabapentin/pregabalin cases had severe profiles at inclusion, but were less severe than the flupirtine cases for HAPTO (0.69g/L; P=0.009), BILI (120 µmol/L; P=0.003) and FibroTest (0.92; P=0.008), respectively, although not for ApoA1 (0.54 g/L; P=0.15).

The APAP cases had the highest ALT (2727 IU/L), AST (647 IU/L) and ActiTest (0.99) and the lowest A2M (1.45 g/L). The A2M was lower in APAP vs. others (1.45 g/L vs. 1.66 G/L). The APAP cases had the lowest miR-122 (−0.07), as expected by the ALT values.

The methotrexate cases had very mild differences compared with normal test ranges [5], and significant differences were expected with regard to the drugs with most severe profiles, i.e., APAP with the highest ALT and flupirtine with the highest BILI. There was no standardized normal median value of miR-122, but the median was higher (7.54) than in the APAP cases (2.12).

The piperacillin cases had the highest GGT median (678 IU/L), significantly higher than in the APAP and methotrexate cases.

The tests were ranked according to their number of significant differences between the 7 groups: HAPTO (n=5), FibroTest (n=5), BILI (n=3), GGT (n=3), ALT (n=3), AST (n=3), ApoA1 (n=3), ActiTest (n=3), and miR-122 (n=1) (FIG. 6). Significant differences in ApoA1 were always associated with differences in BILI and HAPTO. At inclusion, the flupirtine cases had a dramatic increase of BILI associated with a dramatic decrease of HAPTO and ApoA1 compared with the normal ranges observed in cases with methotrexate and "others", but also more surprisingly in comparison with APAP cases, which had the highest level of ALT and a small increase in BILI. miR-122 was not very discriminating at baseline, and only significantly lower in APAP vs. MTX cases.

There were no differences in age, and the interval between the dates of serum sampling. The BMI was higher in the MTX vs. isoniazid cases (30.5 vs. 19.3 kg/m$^2$).

In view of the particular kinetics of ApoA1 and HAPTO, especially shown for flupirtine, it is interesting to include these markers in the logistic function, as it would broaden the sensitivity of the prognosis test.

Example 6. Dynamics of Tests

A total of 81 cases had three repeated measurements of the 10 tests, thus enabling a comparison of the 12-week dynamics between tests, and according to 5 drugs, with at least 3 cases: APAP (n=10), clavulanate (n=4), flupirtine (n=10), isoniazid (n=3), methotrexate (n=3), and the remaining group with fewer cases (n=46) being the "others".

The following tests had significant differences (P<0.0001) between inclusion, 4-8 and 8-12 weeks: ALT, AST, ApoA1, GGT, ActiTest, and miR-122. A2M (P=0.10) and HAPTO (P=0.10) had no significant differences. BILI and FibroTest remained elevated up to 4-8 weeks, thereafter with a significant decrease at 8-12 weeks. GGT seemed more sensitive than BILI with an earlier decrease, which was already significant at 4-8 weeks.

For all drugs, the decrease in ALT, AST and ActiTest were similar, without significant differences. In the methotrexate cases, even though the difference was not significant, there was no decrease in GGT compared with other drugs. In all drugs, A2M remained stable, without any significant differences.

Example 7. Comments

An increase in total bilirubin (BILI) levels along with clinically relevant increases in aminotransferase activity is the signal currently considered most specific for and predictive of severe drug-induced liver injury (DILI) ("Hy's law") [1]. However, the sensitivity of this signal is inadequate for early detection of injury, as the damage has already spread and affected liver function. Changes in aminotransferase activity, particularly in alanine transaminase (ALT), without BILI elevations are more sensitive, but are not sufficiently specific for DILI. Also these current standard biomarkers are not ideal for thoroughly monitoring disease progression and resolution, and they do not allow to clinical outcomes of liver injury to be reliably predicted. The absence of suitable detection methods complicates the development of new and promising medications and is a burden for many approved drugs, which are already used to treat diseases. As a result, there is a clear need for more sensitive, specific, and robust biomarkers of DILI. Improved biomarkers will enable clinical decision-making in terms of safe continuation and discontinuation of drugs during clinical development, as well as in the routine use of marketed drugs.

The primary objective of the experiments reported above was to validate the performance of new investigational biomarkers (or a combination of biomarkers), measured at inclusion, in their prediction of outcomes at twelve weeks (W12). The outcome that was considered of primary importance was the patient's full recovery at W12 after admission with DILI. These new biomarkers have been compared to ALT and BILI, which were the "Standard of Diagnosis", analogous with the "Standard of Care" for treatment [2, 3].

One biomarker of necroinflammatory histological activity, ActiTest, had never been assessed in patients with presumed DILI [4]. ActiTest is a patented panel of six components including ALT transaminases, total bilirubin (Bili) and four other components of FibroTest [5,6]: apolipoprotein-A1 (ApoA1), haptoglobin (HAPTO), alpha-2 macroglobulin (A2M) and gamma-glutamyl transpeptidase (GGT). Since 2001, ActiTest (for activity grading) and FibroTest (for fibrosis staging) have been extensively validated in patients with chronic hepatitis C (CHC), chronic hepatitis B (CHB), non-alcoholic fatty liver disease (NAFLD) and alcoholic liver disease (ALD) [4,5,6,7,8,9].

It was aimed to evaluate the possible prognostic value of ActiTest and each of its components other than BILI and ALT, ApoA1, HAPTO, A2M and GGT, in patients with DILI, using recovery at 12 weeks as the endpoint. It was also assessed whether these components had different serum profiles, possibly in association with different toxicity mechanisms, and whether these could provide earlier or more specific DILI recognition [4,5,6,7,8].

Several objectives were attained through this study.

Primary Objective: Prediction of Recovery

In this study, it was identified for the first time that ApoA1 and HAPTO had significant predictive values for the prediction of recovery at 12 weeks in patients with DILI. This enabled the construction of a new prognostic panel, the DILI-ActiTest, combining ApoA1, HAPTO, A2M and GGT adjusted for gender and age, which had significant predictive value for recovery at 12 weeks, as described above.

ApoA1 and HAPTO are "acute phase reactants" but have already been used since 2001 in patients with chronic liver disease as components of FibroTest and ActiTest for the prediction of fibrosis and necroinflammatory activity [4,7]. Few studies have analyzed the associations between these proteins and acute liver disease. Serum proteomic profiling of acute phase reactants was performed in healthy volunteers receiving APAP, which revealed a significant three-fold down-regulation of ApoA1 in subjects with ALT increase ("ALT responders") compared with ALT non-responders, but no difference before treatment [13].

The results reported here confirmed this negative association in patients with DILI, both for APAP and non-APAP cases and for both ApoA1 and HAPTO.

ApoA1 and HAPTO as Biomarkers of DILI Risk

It was observed that ApoA1 and HAPTO returned to normal values in patients who recovered at 8-12 weeks, and these values were higher than in cases that did not recover.

As the baseline values of these patients before the DILI episode were not available, it is impossible to definitively conclude that these proteins are biomarkers for DILI susceptibility. However, these results were partly in line with those observed in healthy volunteers, prior to APAP treatment, with HAPTO significantly higher in ALT responders vs. non-responders, suggesting an individual risk profile; it then remained significantly up-regulated after repeated APAP treatment for seven days [13].

Diverse functions attributed to ApoA1 and HAPTO could explain these results. The acute phase response induces major changes in HDL functions, since in this context ApoA1 is replaced by other acute-phase proteins, such as serum amyloid A protein, ceruloplasmin, and HAPTO. HDLs are believed to be part of the humoral innate immune system, which helps mammals fight against invading pathogens, due to the presence of different proteins on the HDL molecules, such as ApoA1 and HAPTO-related proteins [17].

HAPTO is a tetrameric glycoprotein, with recent evidence pointing to its function as a chemoatttractant for macrophages [18]. HAPTO deficiency is associated with attenuation of hepatosteatosis and impairment of glucose homeostasis, suggesting this protein has a wider role in liver injury. Acute phase reactants act as protective antioxidants and play a role in the reticuloendothelial system. This system is composed of monocytes and macrophages and is part of the immune system that removes cell debris, as observed in cytolitic hepatitis.

The results above are the first to report A2M values in DILI cases, and it confirms that this protein usually does not vary significantly with acute inflammation, contrary to HAPTO and ApoA1. The only exception (0.31 g/L) was an APAP case with severe malnutrition (albumin 29 g/L), a rare cause of low A2M [14], together with the highest ALT (16,000 I U/L) and AST (31,000 IU/L) levels, as well as the lowest miR-122 (−0.8).

Dynamics of Tests

Analyses of the repeated measurements have identified several specific profiles of tests or drugs. In all cases and regardless of the drug, there was an expected rapid decrease of ALT and AST, which was both highly and negatively correlated with an increase of miR-122. Of the miRNAs, 70% of which originate in the liver, miR-122 has been the most extensively studied. Its level in serum is increased in hepatitis B and C, and non-alcoholic fatty liver disease, and is decreased in hepatocellular carcinoma, fibrosis, cirrhosis and metabolic disorders [19,20,21]. It has previously been reported to be increased in DILI, and has prognostic value when associated with albumin, but no acute phase proteins such as HAPTO or ApoA1 were studied. [22].

There were not enough deaths or transplanted cases in the study to use survival without transplantation as an endpoint. miR-122 added no independent predictive value for recovery, as defined here (data not shown). The higher miRNA serum level in DILI could be a compensatory response to liver injury proportional to necroinflammatory histological activity (as presumed by ALT, AST and ActiTest) that leads to recovery. miR-122 has been implicated in the regulation of 7-alpha-hydroxlyase translation (an enzyme involved in cholesterol metabolism), the regulation of hepatocyte differentiation, and hepatocyte regeneration [23]. Contrary to a previous study, a significant correlation at inclusion between BILI and miR-122 was found, which later became non-significant, as seen on FIG. 7. This discrepancy suggests that caution be used in the interpretation and that repeated measurements need to be included before interpreting the association between biomarkers in DILI.

One unexpected result in the study was the strongest negative correlation of both ApoA1 and HAPTO with BILI during the entire 12-week follow-up (FIG. 7), which was much higher than the expected correlations observed with ALT. The specific mechanisms are unknown, but these results suggest that repression of the synthesis of these proteins is not only associated with an acute phase response with high transaminase levels.

ApoA1 and HAPTO remained significantly higher in cases that recovered versus those that did not recover, from inclusion up to 8-12 weeks, and within the range of normal values. Compared with methotrexate and clavulanate, however, the flupirtine cases had a very peculiar evolution, with an extreme decrease in both ApoA1 and HAPTO levels at inclusion, but with much quicker normalization of ApoA1 compared with HAPTO, which remained low at 8-12 weeks. The number of cases was small, but ApoA1 also seemed to return to normal values later than ALT in the clavulanate cases.

GGT has already been recommended as a sensitive marker of acute cholestasis in DILI [10, 16, 27]. Moreover, elevated levels of endogenous GGT often indicate acute hepatocellular damage, and are thus considered as a pre-clinical and clinical biomarker for hepatotoxicity and hepatic injury. The inclusion of GGT in this study was not associated with recovery, regardless of its definition.

Drugs Profiles According to Tests at Inclusion and During Follow-Up

With the limitations of the sample size but the advantages of repeated measurements, the main original conclusion for drug profiles was the decrease of ApoA1 and HAPTO in the flupirtine cases, a typical non-dose dependent ("immune-allergic") drug [25,26,27], in contrast to APAP, the standard dose-dependent drug, which had higher transaminase levels and the lowest A2M level. The mechanisms underlying these differences remain unknown.

Risk of Fibrosis as Sequela of DILI

As the protocol defined the follow-up for only 12 weeks, the results were limited to two cases out of the 18 that still had a FibroTest >0.48 (presumed fibrosis stage F2) at 8-12 weeks and remained at this stage 30 and 877 days later. These two patients were overweight and the presence of NAFLD was also possible. Therefore, more cases need to be included in the long-term follow-up using validated biomarkers to estimate the fibrosis risk. In our study, the high percentage of false positives for significant fibrosis observed in cases that recovered (75%) using Transient Elastometry TE (versus 0% for FibroTest) suggested using blood tests such as FibroTest, as it is more robust than TE, which is too sensitive to activity and steatosis [24].

Limitations of the Study

The long-term impact of DILI as a risk of fibrosis needs to be assessed in large prospective cohorts. As only two cases were identified, the confounding or associated risk of NAFLD should be ruled out in such small sample.

Several confounding factors were not taken into account, such as variability for the treatment of DILI. N-acetyl cysteine (NAC) was used for APAP DILI, but there was heterogeneity in the prescription of NAC in non-APAP cases, as well as for corticosteroid prescriptions.

This study focuses on the diagnostic and prognostic values of the ActiTest components, ApoA1, HAPTO, A2M and GGT, and not on other biomarkers such as alkaline phosphatase.

Conclusions

The main advantages of the results reported here were the prospective inclusion of well-defined cases with an adjudication committee, and a centralized blood bank. It was possible to demonstrate the predictive value of ApoA1 and HAPTO in DILI, which led to the construction of a test that predicts recovery at 12 weeks.

It was shown, for the first time that concentration of haptoglobin and ApoA1, have kinetics different from these of transaminases, the standard reference for DILI.

Haptoglobin had never been used in a panel for DILI diagnosis. Haptoglobin has been used in panels for predicting fibrosis in chronic liver disease The rational for haptoglobin interest in DILI is a protective effect. Haptoglobin has an anti-oxidant function and a role in the reticuloendothelial system. Monocytes and macrophages remove debris as observe in necro-inflammatory features of acute hepatitis. This protective effect is well established in heme iron recovery, as hemoglobin binds hemoglobin, prevents iron loss in hemolysis and prevents kidney injury.

Apoa1 had never been used in a panel for DILI diagnosis. ApoA1 has been used in panels for predicting fibrosis in chronic liver disease and predicting severe acute alcoholic hepatitis. The rational for apoA1 interest in DILI is a protective effect. During the acute phase response, circulating HDL are charged in serum amyloid A (SAA) and depleted in ApoA1. When ApoA1 is liberated from HDL, it interacts with inflammatory cells such as polymorphonuclear neutrophils (PMN). ApoA1 decreases neutrophil degranulation and superoxyde production. ApoA1 facilitates the adhesive responses of PMN to lipopolysaccharide.

The present invention presented for the first time of a panel including two proteins haptoglobin and ApoA1 in a position of protective biomarkers, without bilirubin and ALT, the classical biomarkers of DILI which are mainly the consequences of the drug injury.

These proteins as suggested by our observations and follow-up could also be non-genetic markers of DILI susceptibility.

The results confirmed that HAPTO, and also suggested that ApoA1, could be non-genetic markers of susceptibility to DILI. The study provided more knowledge about the false positive risks of fibrosis biomarkers related to DILI. After a DILI episode, FibroTest® should not be used to predict fibrosis before 12 weeks; this also applies to liver elasticity as estimated by TE, even after 12 weeks, due to a 75% risk of false positive results.

REFERENCES

[1]. Chalasani N, Bonkovsky H L, Fontana R, Lee W, Stolz A, Talwalkar J, Reddy K R, Watkins P B, Navarro V, Barnhart H, Gu J, Serrano J; United States Drug Induced Liver Injury Network. Features and Outcomes of 899 Patients With Drug-Induced Liver Injury: The DILIN Prospective Study. Gastroenterology. 2015;148:1340-52.e7.

[2]. Matheis K, Laurie D, Andriamandroso C, Arber N, Badimon L, Benain X, Bendjama K, Clavier I, Colman P, Firat H, Goepfert J, Hall S, Joos T, Kraus S, Kretschmer A, Merz M, Padro T, Planatscher H, Rossi A, Schneiderhan-Marra N, Schuppe-Koistinen I, Thomann P, Vidal J M, Molac B. A generic operational strategy to qualify translational safety biomarkers. Drug Discov Today. 2011;16:600-8.

[3]. Robles-Diaz M, Lucena M I, Kaplowitz N, Stephens C, Medina-Cáliz I, González-Jimenez A, Ulzurrun E, Use of Hy's law and a new composite algorithm to predict acute liver failure in patients with drug-induced liver injury. Gastroenterology 2014;147:109-118.e5.

[4]. Poynard T, Munteanu M, Ngo Y, Castera L, Halfon P, Ratziu V, Imbert-Bismut F, Thabut D, Bourliere M, Cacoub P, Messous D, de Ledinghen V. ActiTest accuracy for the assessment of histological activity grades in patients with chronic hepatitis C, an overview using Obuchowski measure. Gastroenterol Clin Biol. 2010;34:388-96.

[5]. Imbert-Bismut F, Messous D, Thibault V, Myers R B, Piton A, Thabut D, Devers, et alL. Intra-laboratory analytical variability of biochemical markers of fibrosis (Fibrotest) and activity (Actitest) and reference ranges in healthy blood donors. Clin Chem Lab Med. 2004;42:323-33.

[6]. Piton A, Poynard T, Imbert-Bismut F, Khalil L, Delattre J, Pelissier E, Sansonetti N, Opolon P. Factors associated with serum alanine transaminase activity in healthy subjects: consequences for the definition of normal values, for selection of blood donors, and for patients with chronic hepatitis C. MULTIVIRC Group. Hepatology. 1998; 27:1213-9.

[7]. Imbert-Bismut F, Ratziu V, Pieroni L, Charlotte F, Benhamou Y, Poynard T; MULTIVIRC Group. Biochemical markers of liver fibrosis in patients with hepatitis C virus infection: a prospective study. Lancet. 2001;357:1069-75.

[8]. Munteanu M, Tiniakos D, Anstee Q, Charlotte F, Marchesini G, Bugianesi E, Trauner M, et al. Diagnostic performance of FibroTest, SteatoTest and ActiTest in patients with NAFLD using the SAF score as histological reference. Aliment Pharmacol Ther. 2016 t;44:877-89.

[9]. Poynard T, Deckmyn O, Munteanu M, Ngo Y, Drane F, Castille J M, Housset C, et al. Awareness of the severity of liver disease re-examined using software-combined biomarkers of liver fibrosis and necroinflammatory activity. BMJ Open. 2015;5:e010017.

[10]. Ozer J, Ratner M, Shaw M, Bailey W, Schomaker S. The current state of serum biomarkers of hepatotoxicity. Toxicology. 2008;245:194-205.

[11]. M'Kada H, Munteanu M, Perazzo H, Ngo Y, Ramanujam N, Imbert-Bismut F, Ratziu et al. What are the best reference values for a normal serum alanine transaminase activity (ALT)? Impact on the presumed prevalence of drug induced liver injury (DILI). Regul Toxicol Pharmacol. 2011;60:290-5.

[12]. Starkey Lewis P J, Dear J, Platt V, Simpson K J, Craig D G, Antoine D J, et al. Circulating microRNAs as potential markers of human drug-induced liver injury. Hepatology. 2011;54:1767-76.

[13]. Borlak J, Chatterji B, Londhe K B, Watkins P B. Serum acute phase reactants hallmark healthy individuals at risk for acetaminophen-induced liver injury. Genome Med. 2013;5:86.

[14]. Poynard T, Munteanu M, Deckmyn O, Ngo Y, Drane F, Messous D, Castille J M, Housset C, Ratziu V, Imbert-Bismut F. Applicability and precautions of use of liver injury biomarker FibroTest. A reappraisal at 7 years of age. BMC Gastroenterol. 2011;11:39.

[15]. Hintze J L. NCSS 2009 User Guide. Number Cruncher Statistical Systems software NCSS, Kaysville, Utah 2009.

[16]. Bell L N, Vuppalanchi R, Watkins P B, Bonkovsky H L, Serrano J, Fontana R J, Wang M, Rochon J, Chalasani N; US Drug-Induced Liver Injury Network (DILIN) Research Group. Serum proteomic profiling in patients with drug-induced liver injury. Aliment Pharmacol Ther. 2012; 35:600-12.

[17]. Montecucco F, Favari E, Norata G D, Ronda N, Nofer J R, Vuilleumier N. Impact of systemic inflammation and autoimmune diseases on apoA-I and HDL plasma levels and functions. Handb Exp Pharmacol. 2015;224:455-82

[18]. Chen W, Lu H, Dutt K, Smith A, Hunt D M, Hunt R C: Expression of the protective proteins hemopexin and haptoglobin by cells of the neural retina. Exp Eye Res 1998, 67:83-93.

[19]. Zhang Y, Jia Y, Zheng R, et al. Plasma microRna-122 as a biomarker for viral-, alcohol-, and chemical related hepatic diseases. ClinChem. 2010;56:1830-1838.

[20]. Starkey Lewis P J, Dear J, Pla V, et al. Circulating microRNAs as potential markers of human drug induced liver injury. Hepatology. 2011;54:1767-1776.

[21]. Wang Y, Chen T, Tong W. miRNAs and their application in drug induced liver injury. Biomark Med. 2014;8:162-172.

[22]. Russo M W, Steuerwald N, Norton H J, Anderson W E, Foureau D, Chalasani N, Fontana R J, Watkins P B, Serrano J, Bonkovsky H L. Profiles of miRNAs in serum in severe acute drug induced liver injury and their prognostic significance. Liver Int. 2016 Nov. 12.

[23]. Starckx S, Batheja A, Verheyen G R, et al. Evaluation of miR-122 and other biomarkers in distinct acute liver injury in rats. Toxicol Pathol. 2013;41:795-804.

[24]. Friedrich-Rust M, Poynard T, Castera L. Critical comparison of elastography methods to assess chronic liver disease. Nat Rev Gastroenterol Hepatol. 2016;13:402-11.

[25]. Powell-Jackson P, Williams R. Use of flupirtine maleate as an analgesic in patients with liver disease. Br J Clin Pract 1985; 39: 63-6.

[26]. Methling K, Reszka P, Lalk M, Vrana O, Scheuch E, Siegmund W, Terhaag B, Bednarski P J. Investigation of the in vitro metabolism of the analgesic flupirtine. Drug Metab Dispos. 2009;37:479-93.

[27]. Zhang et al. A two-photon fluorescent sensor revealing drug-induced liver injury via tracking y-glutamyltranspeptidase (GGT) level in vivo. Biomaterials. 2016 February; 80:46-56.

The invention claimed is:

1. A method for assessing and treating Drug-Induced-Liver-Injury (DILI) in a patient receiving a drug comprising:
   (a) measuring markers present in a blood, serum, or plasma sample from the patient to determine concentrations for the markers, wherein the markers are selected from of ApoA1 (Apolipoprotein A-I), A2M (a2-macroglobulin), GGT (gammaglutamyl transpeptidase), and Haptoglobin;
   (b) assigning a value of 0 if the patient is female or assigning a value of 1 if the patient is male;
   (c) obtaining the patient's age;
   (d) combining the concentrations of (a), the value of (b), and the age of (c) through a logistic regression function and obtaining an end-result value,
   wherein
      the logistic regression function is 0.605+0.027×Age (years)+1.197×ApoA1 (g/L)−1.31×LogA2m (g/L)−1.011×LogGGT (IU/L)+0.24×LogHaptoC (g/L)−0.44×Sex (0 for women, 1 for men);
   (e) assessing the end-result value to identify a patient at risk for developing acute liver failure, wherein the patient is at risk for developing acute liver failure when the end-result value is above 0.75; and
   (f) treating the patient at risk for developing acute liver failure by stopping the patient at risk for developing acute liver failure from receiving the drug.

2. A method for assessing and treating Drug-Induced-Liver-Injury (DILI) in a patient receiving a drug comprising:
   (a) measuring markers present in a blood, serum, or plasma sample from the patient to determine values concentrations for the markers, wherein the markers are selected from the group consisting of ApoA1 (Apolipoprotein A-1), A2M (a2-macroglobulin), GGT (gammaglutamyl transpeptidase), and Haptoglobin;
   (b) assigning a value of 0 if the patient is female or assigning a value of 1 if the patient is male;
   (c) obtaining the patient's age;
   (d) combining the concentrations of (a), the value of (b), and the age of (c) through a logistic regression function and obtaining an end-result value,
   wherein the logistic regression function is 0.605+0.027×Age (years)+1.197×ApoA1 (g/L)−1.31×LogA2m (g/L)−1.011×LogGGT (IU/L)+0.24×LogHaptoC (g/L)−0.44×Sex (0 for women, 1 for men);
   (e) assessing the end-result value to identify a patient at risk for developing acute liver failure, wherein the patient is at risk for developing acute liver failure when the end-result value is above 0.75; and
   (f) treating the patient at risk for developing acute liver failure with a liver transplant.

* * * * *